United States Patent
Steuer et al.

(10) Patent No.: US 6,746,407 B2
(45) Date of Patent: Jun. 8, 2004

(54) METHOD OF MEASURING TRANSCUTANEOUS ACCESS BLOOD FLOW

(75) Inventors: Robert R. Steuer, Pleasant View, UT (US); David A. Bell, Farmington, UT (US); David R. Miller, Morgan, UT (US)

(73) Assignee: Hema Metrics, Inc., Kaysville, UT (US)

( * ) Notice: Subject to any disclaimer, the term of this patent is extended or adjusted under 35 U.S.C. 154(b) by 11 days.

(21) Appl. No.: 09/750,122

(22) Filed: Dec. 29, 2000

(65) Prior Publication Data

US 2002/0128545 A1 Sep. 12, 2002

(51) Int. Cl.$^7$ ................................................. A61B 5/00
(52) U.S. Cl. ............................................. 600/505; 604/4
(58) Field of Search ................................ 600/504, 505; 73/861; 604/4

(56) References Cited

U.S. PATENT DOCUMENTS

| | | |
|---|---|---|
| 3,638,640 A | 2/1972 | Shaw |
| 3,880,151 A | 4/1975 | Nilsson et al. |
| 4,014,321 A | 3/1977 | March |
| 4,081,372 A | 3/1978 | Atkin et al. |
| 4,086,915 A | 5/1978 | Kofsky et al. |
| 4,167,331 A | 9/1979 | Nielsen |

(List continued on next page.)

FOREIGN PATENT DOCUMENTS

| | | |
|---|---|---|
| EP | 104772 B1 | 4/1984 |
| EP | 160768 B1 | 11/1985 |
| EP | 0 529 412 | 3/1993 |
| EP | 0 928 614 | 7/1999 |
| WO | WO 86/06946 | 12/1986 |
| WO | WO 89/01758 | 3/1989 |
| WO | WO 93/06456 | 4/1993 |

OTHER PUBLICATIONS

J.P. Payne and J.W. Severinghaus, Eds., *Pulse Oximetry*, Chapters 1 and 2 (©1986).

John D. Bower and Thomas G. Coleman, *Circulatory Function During Chronic Hemodialysis*, vol. XV Trans. Amer. Soc. Artif. Int. Organs, 1969, 373–377.

(List continued on next page.)

*Primary Examiner*—Robert L. Nasser
(74) *Attorney, Agent, or Firm*—Jacobson Holman PLLC

(57) ABSTRACT

Indicator dilution techniques are used to measure vascular access flow rates during routine hemodialysis. A bolus injection port is used to infuse a specific volume ($V_i$) of an indicator diluent, such as saline or dye, into the patient cardiovascular circuit by one of the following:

1. Needle injection of a known volume (bolus) of indicator diluent directly into the access site in the presence or absence of the hemodialysis circuit.
2. Infusion of an indicator diluent into the arterial, venous line upstream of the venous needle.
3. Turning the ultrafiltration of the dialysis delivery system from OFF to ON and OFF again over a predetermined time period.
4. In a hemodialysis circuit, turning on the hemodialysis pump and using the priming saline volume as a single saline bolus.

A transdermal sensor is used to measure the percent change in a blood parameter. The sensor is positioned directly over the vascular access site a prescribed distance downstream of the injection site and upstream of the access-vein connection. The sensor employs emitter and detector elements at multiple spacings ($d_1$, $d_2$) for the purpose of measuring the bulk absorptivity ($\alpha$) of the area immediately surrounding and including the access site, and the absorptivity ($\alpha_o$) of the tissue itself.

9 Claims, 12 Drawing Sheets

U.S. PATENT DOCUMENTS

| | | | |
|---|---|---|---|
| 4,181,610 | A | 1/1980 | Shintani et al. |
| 4,223,680 | A | 9/1980 | Jöbsis |
| 4,266,554 | A | 5/1981 | Hamaguri |
| 4,295,470 | A | 10/1981 | Shaw et al. |
| 4,416,285 | A | 11/1983 | Shaw et al. |
| 4,446,871 | A | 5/1984 | Imura |
| 4,653,498 | A | 3/1987 | New, Jr. et al. |
| 4,655,225 | A | 4/1987 | Dahne et al. |
| 4,685,464 | A | 8/1987 | Goldberger et al. |
| 4,714,080 | A | 12/1987 | Edgar, Jr. et al. |
| 4,770,179 | A | 9/1988 | New et al. |
| 4,805,623 | A | 2/1989 | Jöbsis |
| 4,819,752 | A | 4/1989 | Zelin |
| 4,821,734 | A | 4/1989 | Koshino |
| 4,824,242 | A | 4/1989 | Frick et al. |
| 4,825,872 | A | 5/1989 | Tan et al. |
| 4,825,879 | A | 5/1989 | Tan et al. |
| 4,832,484 | A | 5/1989 | Aoyagi et al. |
| 4,863,265 | A | 9/1989 | Flower et al. |
| 4,867,557 | A | 9/1989 | Takatani et al. |
| 4,920,972 | A | 5/1990 | Frank et al. |
| 4,925,299 | A | 5/1990 | Meisberger et al. |
| 5,028,787 | A | 7/1991 | Rosenthal et al. |
| 5,035,243 | A | 7/1991 | Muz |
| 5,048,524 | A | 9/1991 | Bailey |
| 5,054,487 | A | 10/1991 | Clarke |
| 5,057,695 | A | 10/1991 | Hirao et al. |
| 5,058,587 | A | 10/1991 | Kohno et al. |
| 5,059,394 | A | 10/1991 | Phillips et al. |
| 5,066,859 | A | 11/1991 | Karkar et al. |
| 5,092,836 | A | 3/1992 | Polaschegg |
| 5,101,825 | A | 4/1992 | Gravenstein et al. |
| 5,111,817 | A | 5/1992 | Clark et al. |
| 5,127,406 | A | 7/1992 | Yamaguchi |
| 5,137,023 | A | 8/1992 | Mendelson et al. |
| 5,158,091 | A | 10/1992 | Butterfield et al. |
| H1114 | H | 12/1992 | Schweitzer et al. |
| 5,193,543 | A | 3/1993 | Yelderman |
| 5,237,999 | A | 8/1993 | von Berg |
| 5,285,783 | A | 2/1994 | Secker |
| 5,351,686 | A | 10/1994 | Steuer et al. |
| 5,456,253 | A | 10/1995 | Steuer et al. |
| 5,499,627 | A | 3/1996 | Steuer et al. |
| 5,520,177 | A | 5/1996 | Ogawa et al. |
| 5,551,422 | A | 9/1996 | Simonsen et al. |
| 5,595,182 | A * | 1/1997 | Krivitski ............... 600/504 |
| 5,785,657 | A | 7/1998 | Breyer et al. |
| 5,797,841 | A | 8/1998 | Delonzor et al. |
| 5,803,908 | A | 9/1998 | Steuer et al. |
| 5,817,009 | A | 10/1998 | Rosenheimer et al. |
| 6,041,246 | A | 3/2000 | Krivitski et al. |
| 6,117,099 | A * | 9/2000 | Steuer et al. ............ 604/4 |
| 6,153,109 | A | 11/2000 | Krivitski |
| 6,167,765 | B1 * | 1/2001 | Weitzel ............... 600/454 |
| 6,189,388 | B1 * | 2/2001 | Cole et al. ............ 73/861.07 |
| 6,210,591 | B1 * | 4/2001 | Krivitski ............... 73/861 |
| 6,452,371 | B1 * | 9/2002 | Brugger ............... 73/861.07 |

OTHER PUBLICATIONS

Larry Reynolds, C. Johnson, A. Ishimaru, *Diffuse reflectance from a finite blood medium: applications to the modeling of fiber optic catheters*, Sept. 1976, vol. 15, No. 9, Applied Optics, pp. 2059–2067.

R.N. Greenwood, C, Aldridge, L. Goldstein, L.R.I. Baker and W.R. Cattell, *Assessment of arteriovenous fistulae from pressure and thermal dilution studies: clinical experience in forearm fistulae*, Clinical Nephrology, vol. 23, No. 4–1985, pp. 189–197.

R.N. Greenwood, C. Aldridge and W.R. Cattell, *Serial blood water estimations and in–line blood viscometry: the continuous measurement of blood volume during dialysis procedures,* Clinical Science (1984)66, pp. 575–583.

C. Aldridge, R.N. Greenwood, W.R. Cattell and R.V. Barrett, *The assessment of arteriovenous fistulae created for haemodialysis from pressure and thermal dilution measurements*, Journal of Medical Engineering & Technology, vol. 8, No. 3 (May/Jun.), pp. 118–124.

N.M. Krivitski et al., "Saline Release Method to Measure Access Flow (AF) by Ultrasound Dilution during Hemodialysis," *JASN Abstracts*,8:164A, 1997.

N.M. Krivitski, "Novel method to measure access flow during hemodialysis by ultrasound velocity dilution technique," *ASAIO J* 41:M741–M745, 1995.

T.A. Depner and N.M. Krivitski, "Clinical measurement of blood flow in hemodialysis access fistulae and grafts by ultrasound dilution," *ASAIO J* 41:M745–M749, 1995).

D. Yarar et al., "Ultrafiltration method for measuring vascular access flow rates during hemodialysis,"*Kidney Int.*, 56: 1129–1135 (1999).

Joseph M. Schmitt, Fred G. Mihm and James Meindl, *New Methods for Whole Blood Oximetry*, Annals of Biomedical Engineering, vol., 14, pp. 35–52, 1986.

Mark R. Arnfield, J. Tulip and Malcolm McPhee, *Optical Propagation in Tissue With Anisotropic Scattering*, IEEE Transactions on Biomedical Engineering, vol. 35, No. 5, May 1988, pp. 372–381.

N.M. Krivitski, "Theory and validation of access flow measurements by dilution technique during hemodialysis," *Kidney Int* 48:244–250, 1995.

L. Goldstein, L. Pavitt, R.N. Greenwood, C. Aldridge, L.R.I. Baker and W.R. Cattell, *The Assessment of Areteriovenous Fistulae From Pressure and Recirculation Studies*, ProcEDTNA–ERCA (1985) vol. 14., pp. 207–215.

R.N. Greenwood, C. Aldridge, L. Goldstein, L.R.I. Baker and W.R. Cattell, *Assessment of Arteriovenous Fistulas From Pressure and Recirculation Studies: Clinical Experience In 215 Upper Limb Fistulas*, ProcEDTNA–ERA(1985) vol. 22, pp. 296–302.

Joseph M. Schmitt, James D. Meindl and Frederick G. Mihm, *An Integrated Circuit–Based Optical Sensor for In Vivo Measurements of Blood Oxygenation*, IEEE Transactions On Biomedical Engineering, vol. BME–33, No. 21, Feb. 1986, pp. 98–107.

* cited by examiner

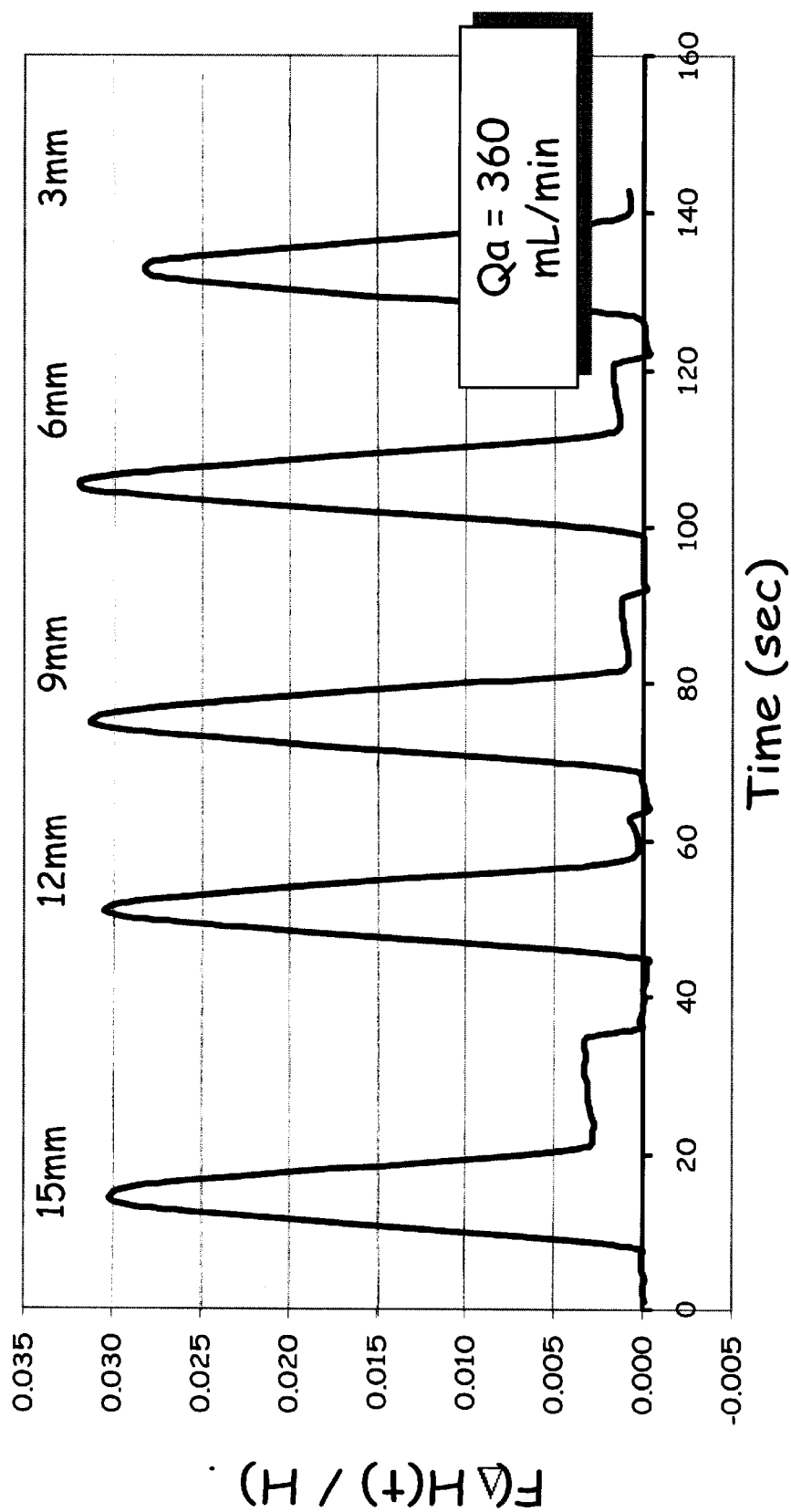
Figure 5. Skin Thickness, Access Depth

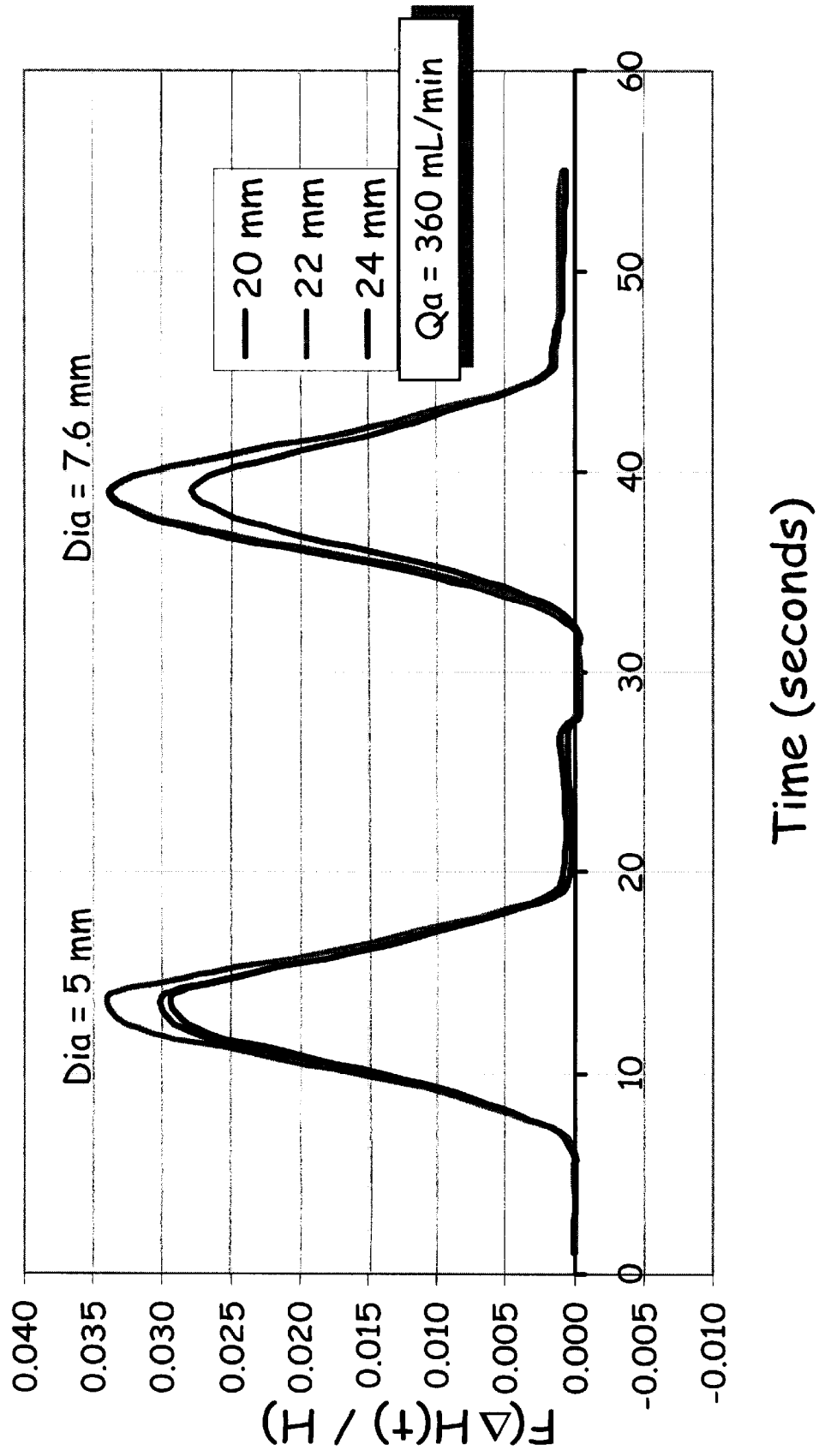

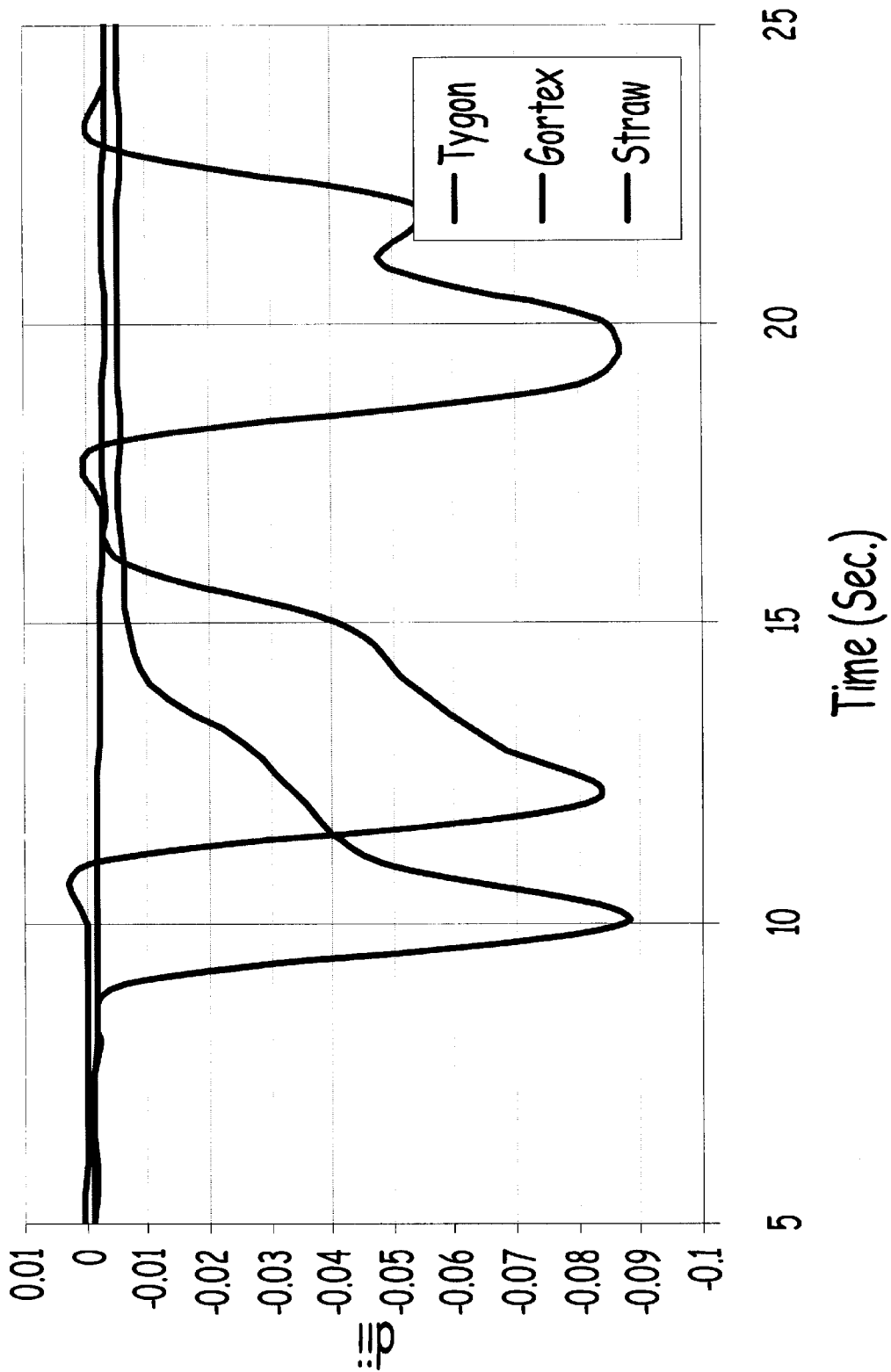

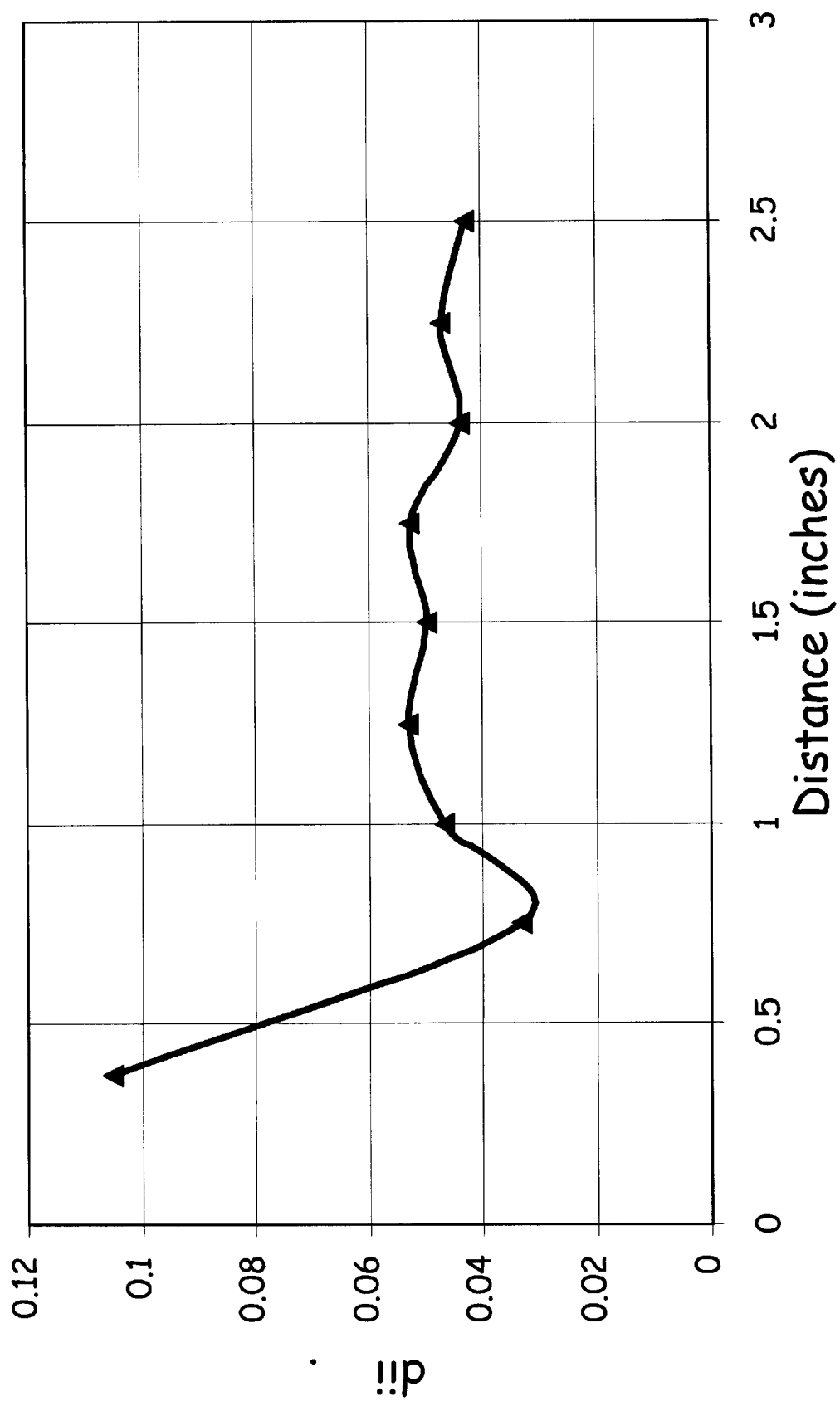
Figure 8. Distance from Needle

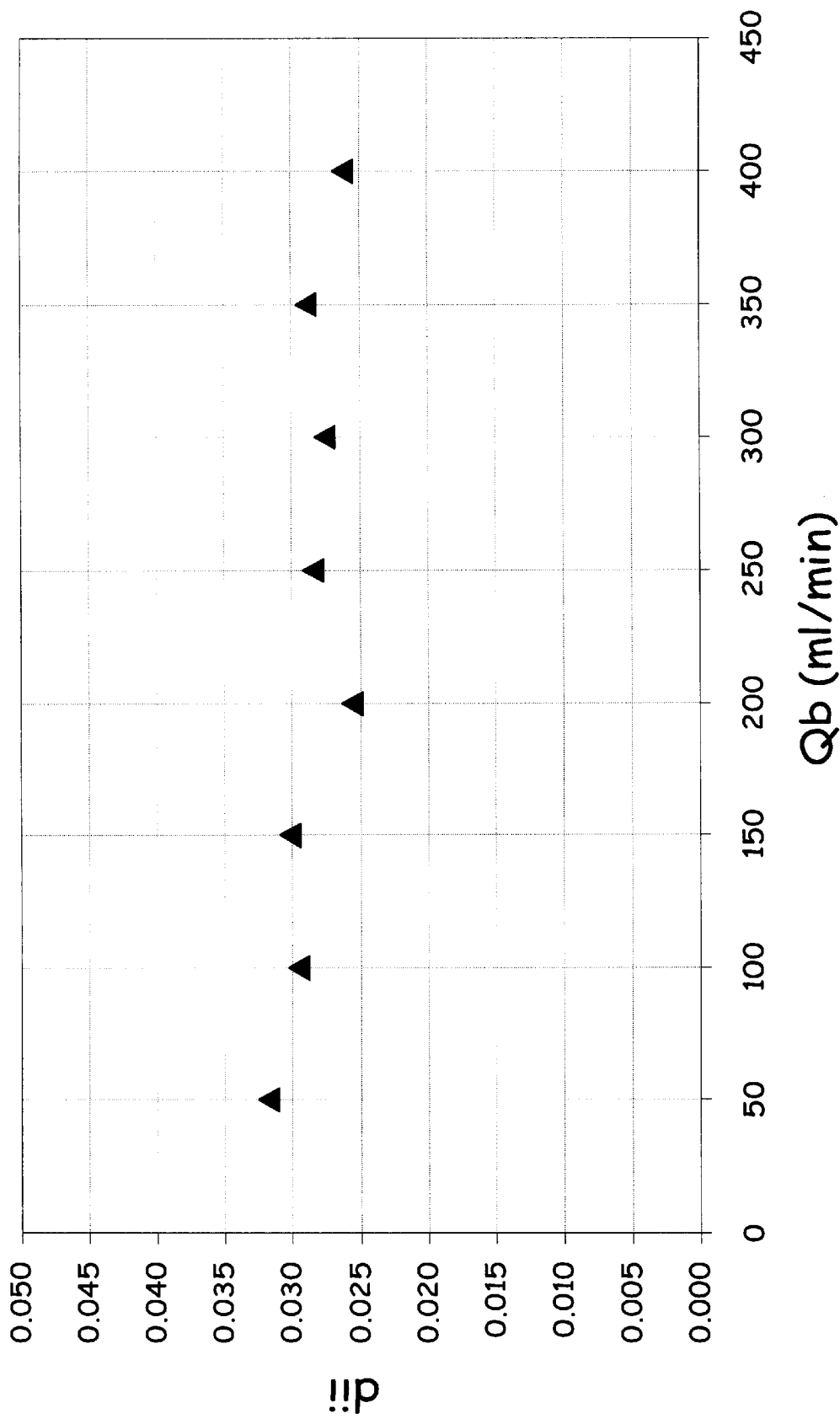

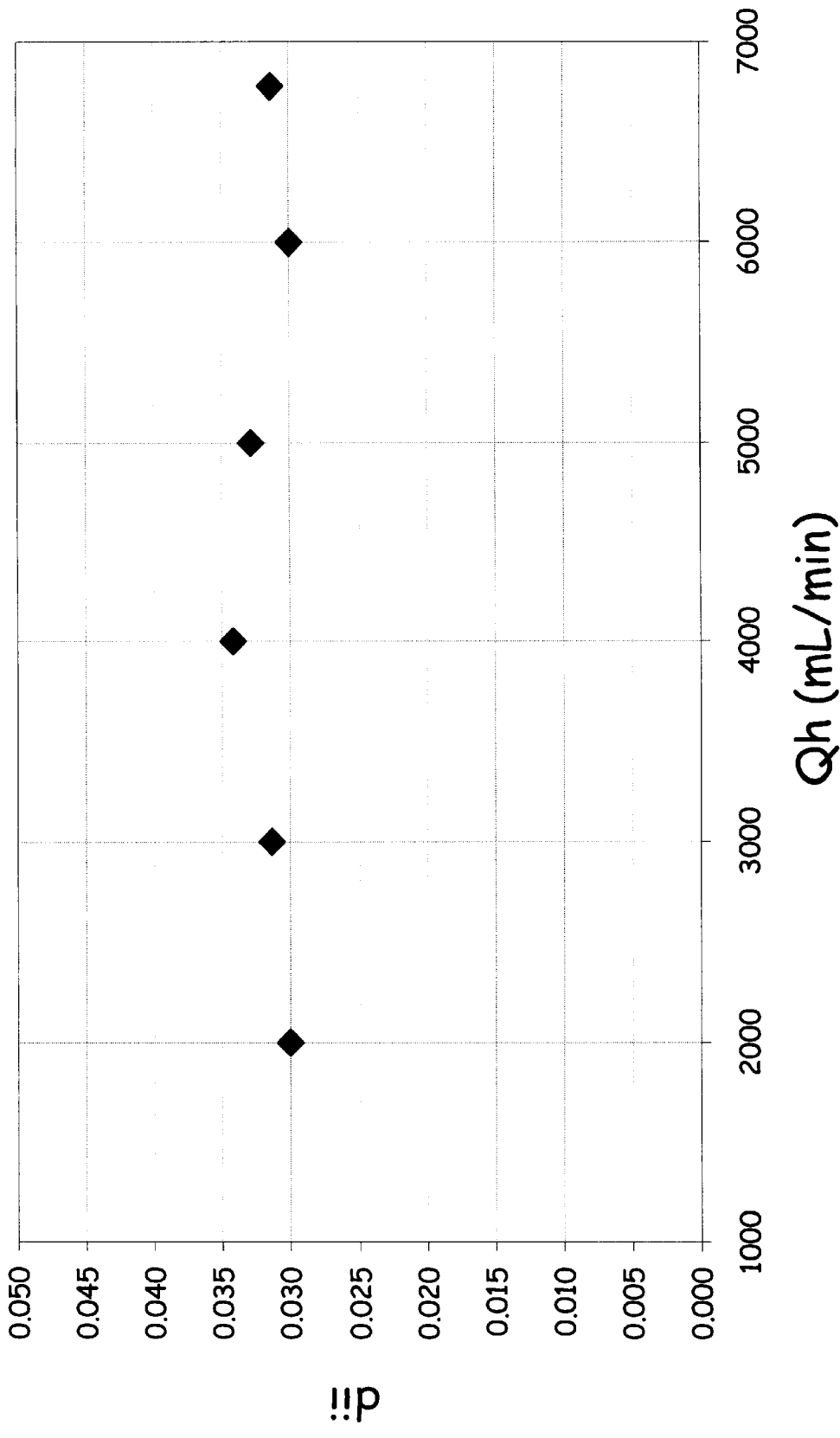
Figure 10. Different Cardiac Pump Rates

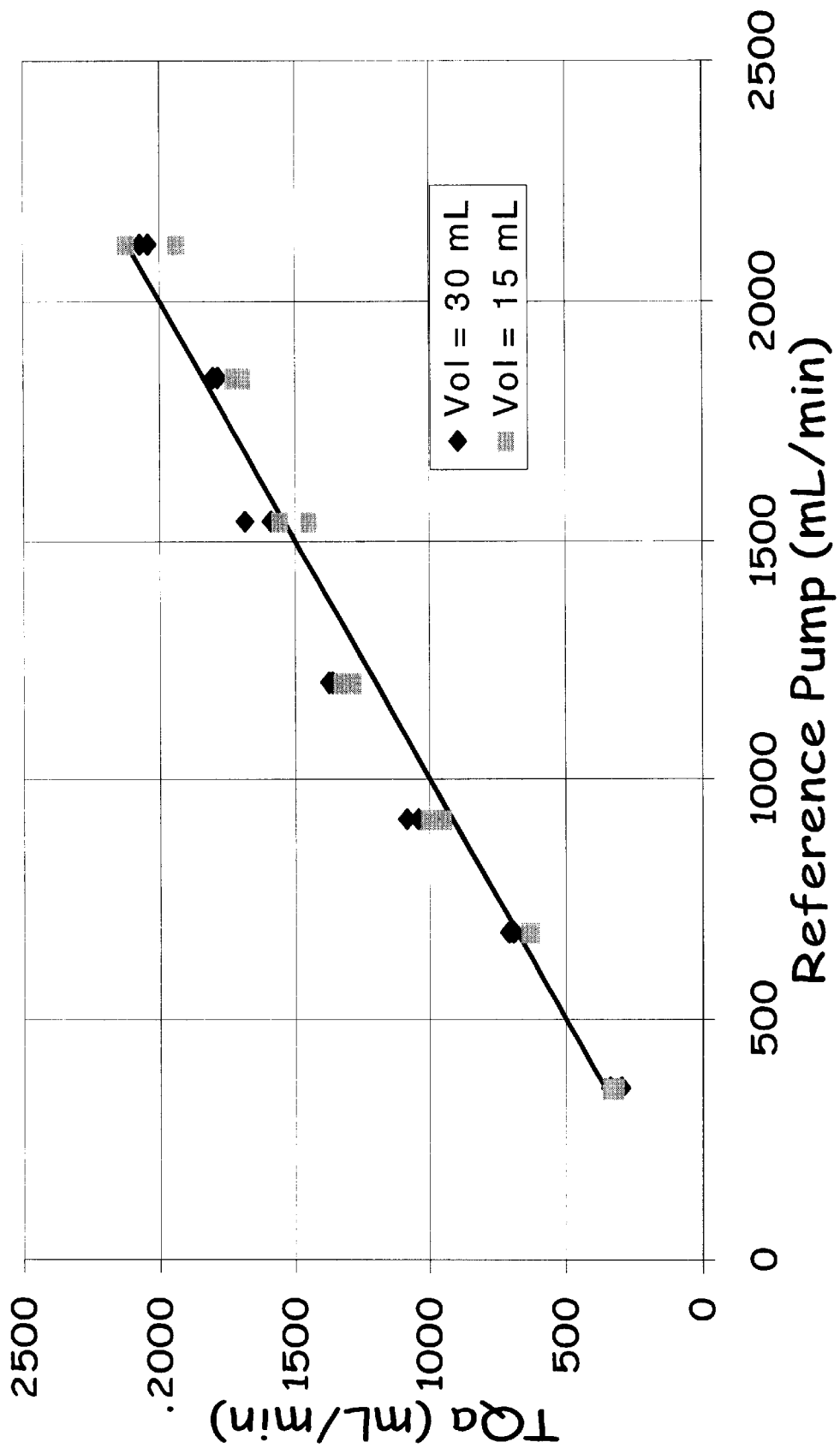

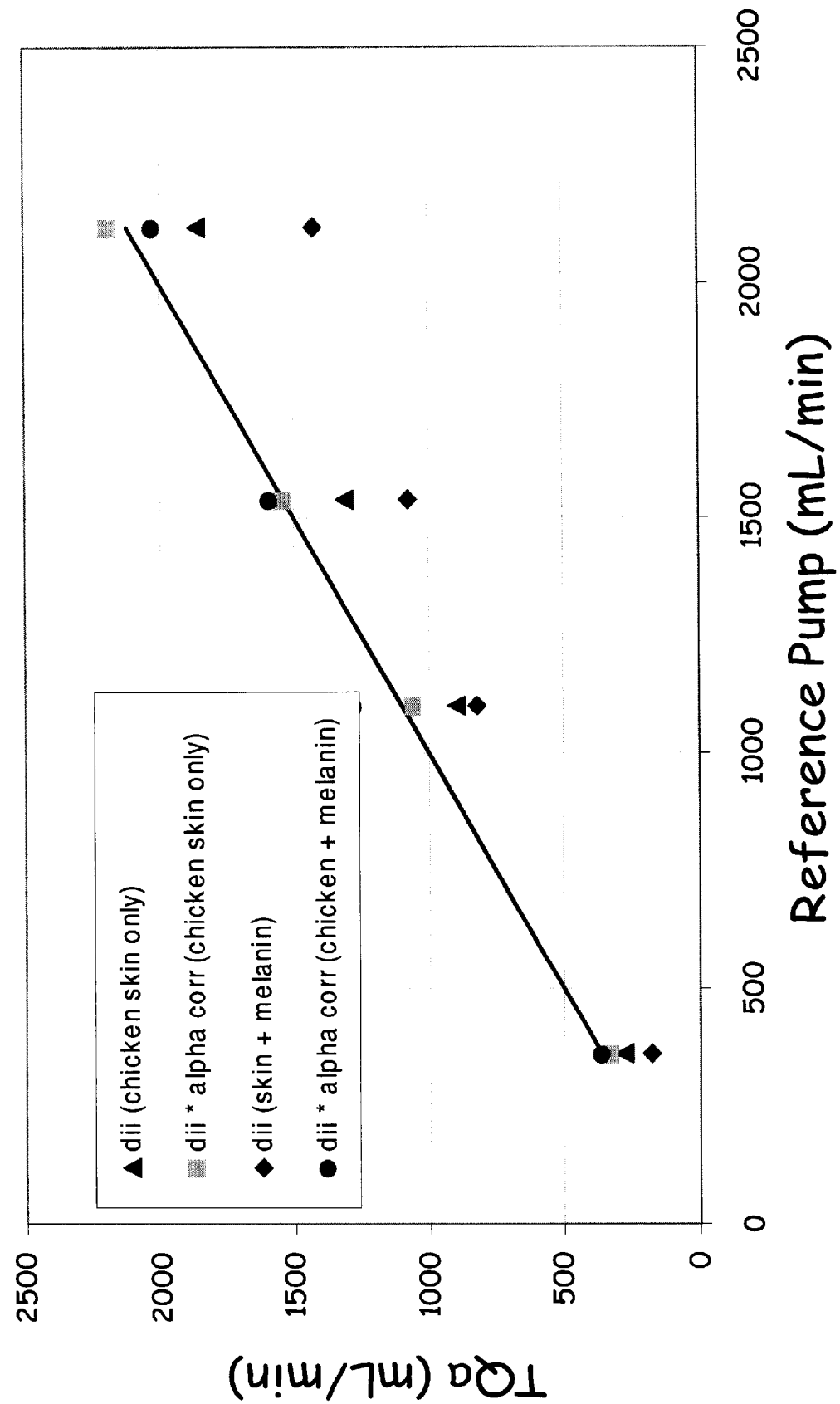
Figure 12. Different Melanin Content

METHOD OF MEASURING TRANSCUTANEOUS ACCESS BLOOD FLOW

BACKGROUND OF THE INVENTION

1. Field of the Invention

The present invention relates to a method for transcutaneously measuring access blood flow. More specifically, the invention relates to a method for measuring access blood flow through the optical measurement of percentage change in a blood parameter and application of the Ficke dilution principle.

2. Related Art

Modern medical practice utilizes a number of procedures and indicators to assess a patient's condition especially in the dialysis setting. Hemodialysis is a process wherein an artificial kidney is required to function in the place of the patient's normal kidney in order to remove certain biologic waste products. When the human kidney no longer functions correctly removing waste products such as urea, potassium, and even excess water, blood must be removed from the patient via blood tubing lines and filtered through an artificial kidney or dialyzer. In this process blood is passed through the dialyzer, cleansed, then returned to the normal circulatory system of the patient. Access to the patient's circulatory system is achieved through the use of a surgically implanted shunt or fistula (access). This "access site" is typically located in the arm, leg, or neck of the patient. Typically needles are placed into the access in such a way as to facilitate the easy removal of blood on the "arterial" or upstream side of the dialyzer and typically return the purified blood downstream of the first needle placement on the "venous" side. Unfortunately, in many cases the access will clot or "stenos" over time. This results in decreased blood flow through the access site which ultimately necessitates either angioplasty or a surgical replacement of the shunt. As the access flow ceases or "clots off" part of the purified dialyzed blood is forced to flow back into the arterial withdrawal site and, hence, recirculates only to be dialyzed again; this is termed "access recirculation".

Access Blood Flow (ABF, represented by the variable $Q_a$) is the rate at which blood passes through an arteriovenous (AV) graft or fistula. Poor or low $Q_a$ rates are generally indicative of hemo-dynamically significant access stenosis and/or thrombosis, which can reduce the adequacy of dialysis therapy and endanger the patient. In 1997 Dialysis Outcomes Quality Initiative (DOQI) Guidelines, the National Kidney Foundation (NKF) sets forth both the rationale and the procedural guidelines for the monitoring and maintenance of AV grafts and fistulas. These guidelines suggest that regular assessment of ABF may be predictive of access stenosis, which in turn may facilitate early intervention, thereby reducing the rate of thrombosis and loss.

NKF-DOQI Guidelines clearly identify access blood flow as a preferred method of monitoring AV grafts and fistulas: "Sequential, timely, repetitive measurement of access flow is the preferred method for monitoring AV grafts", and "Flow measurements should be used when available to monitor for stenosis and thrombosis in AV fistulae." NKF-DOQI Pocket Summary, Clinical Practice Guidelines for Vascular Access: Guideline 10,11.

Lindsay and Leypoldt state, "Reductions in access blood flow rates if recognized may mandate reductions in QB and lead to difficulty in delivering adequate dialysis; if unrecognized these reductions can lead to the phenomenon of access recirculation, which will significantly decrease the efficiency of the hemodialysis treatment. Furthermore, such reductions may herald the problem of acute access thrombosis. It seems ideal, therefore, to monitor access blood flow." Lindsay R, Leypoldt J: Monitoring Vascular Access Flow. Advances In Renal Replacement Therapy, Vol. 6, No. 3 (July), 1999: pp. 273–277.

Blood flow, Q, measured by the so-called Ficke dilutional techniques, has been described by A. C. Guyton, Textbook of Medical Physiology, Sixth Edition, pg. 287, 1981, wherein Q equals the volume of the injected diluent divided by the mean concentration of the diluent times the duration of the passage of the diluent through the vessel. A dilution curve is obtained by continuously monitoring changes in a given physical parameter of the blood over the time period of the injection. The change in the concentration of either the diluent (or the media) is measured over time.

Access Blood Flow (ABF) measurement is an area of concern in hemodialysis since it is a good indicator of access viability. Recent methods of determining ABF have included Doppler imaging, reversed line recirculation, and $$\frac{\Delta H}{H}$$ (the percentage change in hematocrit through the access site).

The time, cost, and/or dialysis line reversal requirements of these methods have greatly limited their wide spread use and routine clinical applicability. With the exception of Doppler, ABF methods require the patient to be on dialysis and unencumbered by intradialytic activity such as blood pressure assessment or eating, further reducing flexibility in measurement. Conversely, Doppler measurements remain limited in accuracy due to uncertainty in measuring access size and cross-sectional area.

It is to the solution of these and other problems that the present invention is directed.

SUMMARY OF THE INVENTION

It is therefore a primary object of the present invention to provide a straightforward method of determining ABF, $Q_a$, using an optical sensor placed on the skin directly over the access site.

It is another object of the present invention to provide a transcutaneous method of ABF measurement that is not affected by size and/or depth of the access site, placement of the dialysis needles, pump speed variations, skin color, tissue composition, or access site location and type.

It is another object of the invention to provide a method of measuring a parameter transcutaneously downstream of a site where an indicator diluent is injected.

It is another object of the invention to provide a method of measuring a parameter transcutaneously in a perturbed system downstream of a site where the perturbation is introduced.

These and other objects of the invention are achieved by use of indicator dilution techniques to measure vascular access flow rates during routine hemodialysis, as well as in a clinic, before and/or after hemodialysis. A bolus injection port is used to infuse a specific volume ($V_i$) of an indicator diluent, such as saline or dye, into the patient cardiovascular circuit by one of the following:

1. Needle injection of a known volume (bolus) of indicator diluent directly into the access site in the presence or absence of the hemodialysis circuit.
2. Infusion of an indicator diluent into the arterial or venous needle or line upstream of the detector.

3. Turning the ultrafiltration of the dialysis delivery system from OFF to ON and OFF again over a predetermined time period.
4. In a hemodialysis circuit, turning on the hemodialysis pump and using the priming saline volume as a single saline bolus.

A transdermal optical sensor is used to measure the percent change in a blood parameter. The sensor is positioned directly over the vascular access site a prescribed distance downstream of the injection site and upstream of the access-vein connection in the case of grafts. The sensor employs complementary emitter and detector elements at multiple spacings ($d_1$, $d_2$) for the purpose of measuring the bulk absorptivity ($\alpha$) of the area immediately surrounding and including the access site, and the absorptivity ($\alpha_o$) of the tissue itself.

In one aspect of the invention, the optical sensor system comprises an LED of specific wavelength and a complementary photodetector. A wavelength of 805 nm–880 nm, which is near the known isobestic wavelength for hemoglobin, is used.

When the sensor is placed on the surface of the skin, the LED illuminates a volume of tissue, and a small fraction of the light absorbed and back-scattered by the media is detected by the photodetector. The illuminated volume as seen by the photodetector can be visualized as an isointensity ellipsoid, as individual photons of light are continuously scattered and absorbed by the media. Because a wavelength of 805 nm–880 nm is used, hemoglobin of the blood within the tissue volume is the principal absorbing substance. The scattering and absorbing characteristics are mathematically expressed in terms of a bulk attenuation coefficient ($\alpha$) that is specific to the illuminated media. The amount of light detected by the photodetector is proportional via a modified Beer's law formula to the instantaneous net $\alpha$ value of the media.

When the volume of tissue illuminated includes all or even part of the access, the resultant $\alpha$ value includes information about both the surrounding tissue and the access itself. In order to resolve the signal due to blood flowing within the access from that due to the surrounding tissues, the sensor system illuminates adjacent tissue regions on either side of the access. Values of $\alpha_o$ for tissue regions not containing the access are then used to normalize the signal, thus providing a baseline from which can be assessed in access hematocrit in the access blood flowing directly under the skin.

In the case that hematocrit is the monitored parameter, these values are then related to the percentage change of the parameter by the relationship:

$$F\left(\frac{\Delta H}{H}\right) = \frac{\frac{di}{i}}{\left(d - \frac{1}{\alpha}\right)(\alpha^2 - \alpha_o^2)},$$

where i is defined from a modified Beer's law as:

$$I \approx I_o A e^{-\alpha d},$$

where $A \approx \alpha$

More specifically, the diluent bolus is injected into the access site at an average flow rate of $Q_i$. Since the hematocrit of the indicator solution is zero, the red blood cell (RBC) mass does not change. The transcutaneous access blood flow ($TQ_a$) differential equation of state may be re-written in either a transient formulation, $$Q_a = \frac{V_i}{\int F\left(\frac{\Delta H}{H}\right) dt}, \text{ where } \frac{\Delta H}{H} = \text{function of time}$$

or time dependent or steady flow formulation. The steady flow form of the $TQ_a$ differential equation is obtained by assuming uniform and steady flow rates over the analysis time period, and is written as $$Q_a = \frac{Q_i}{F\left(\frac{\Delta H}{H}\right)}$$

In both cases, the quantity $$F\left(\frac{\Delta H}{H}\right)$$

is measured as the indicator bolus is injected into the system. If the bolus injection rate $Q_i$ is uniform and constant, then the access flow $Q_a$ may be determined from the steady flow formulation. Conversely, if the system remains dynamic and the bolus injection rate is uncertain or uncontrollable, then the transient solution must be used to determine $Q_a$.

The percentage change in blood parameters (both macroscopic and microscopic) passing through the access site can be measured in a variety of ways. Macroscopic parameters such as bulk density or flow energy can be measured by ultrasonic, temperature, or conductivity means. Microscopic parameters (sometimes called "physiologic or intrinsic" parameters) such as hematocrit or red cell oxygen content are measured by optical means. In both cases, the measurement relies on the quantity $$\frac{di}{i}$$

when saline is injected. Thus, the method in accordance with the present invention can also be applied to the measurement of macroscopic parameters (percent change in density, temperature, conductivity, or energy) using ultrasonic, temperature, or conductivity sensors; and to the measurement of microscopic parameters like hematocrit using an optical sensor.

In the measurement of both macroscopic and microscopic blood parameters, it is necessary to differentiate the access site, and parameter changes therein, from the surrounding tissue structure. The method in accordance with the present invention utilizes a transdermal sensor incorporating photoemitters and photodetectors positioned directly over the access site itself and is based upon optical back-scattering of monochromatic light ($\lambda$=805 nm–880 nm) from the blood flow in the access site and the surrounding tissues, so that it is not limited to the extracorporeal circuit.

Light back-scattered from a turbid tissue sample follows the modified form of Beer's Law, $$I \approx I_o A e^{-\alpha d}, A \approx \alpha$$

A transcutaneously measured $\alpha$ value is a prorated composite measure of all the absorption and scattering elements contained within the illuminated volume or "glowball" of the emitter source, and typically includes the effects of tissue, water, bone, blood, and in the case of hemodialysis patients, the access site. The effects of absorption and scattering of the access site are separated from that of surrounding tissue structure by taking measurements in areas near but not including the access site. If the tissue is more or less homogeneous, it is only necessary to make a single, non-access site reference $\alpha_o$ measurement. On the other hand, if a gradient in $\alpha_o$ exists in the area of interest, multiple measurements are made to establish the nature of the gradient and provide an averaged estimate of $\alpha_o$.

The value of $$\frac{\Delta H}{H}$$

is defined as the time derivative of intensity i, normalized by i. To determine $$\frac{di}{i},$$

a baseline intensity (taken in the absence of a bolus) is first measured to establish a reference. The intensity is then measured as a time varying signal. The quantity $$\frac{di}{i}$$

is then calculated as $$\frac{di}{i} = \frac{I_{baseline} - I(t)}{I_{baseline}}$$

The value $$F\left(\frac{\Delta H}{H}\right)$$

consequently is:

$$F\left(\frac{\Delta H}{H}\right) = \frac{\frac{di}{i}\alpha}{\left(d - \frac{1}{\alpha}\right)(\alpha^2 - \alpha_o^2)}$$

Since d is fixed and known, $$\frac{di}{i},$$

$\alpha$ and $\alpha_o$ are computed by the equations:

$$\frac{di}{i} = \frac{I_{baseline} - I(t)}{I_{baseline}}$$

and $$\alpha \approx \frac{-Ln\left(\frac{I_{measured}}{I_o}\right)}{d}$$

or from:

$$I \approx I_o \alpha e^{-\alpha d},$$

where $\alpha$ is solved in polynomial form.
where access size and/or volume or depth dependence are not factors in either the transient or the steady state formulation of $Q_a$.

It is another object of the invention to provide a method of measuring a parameter transcutaneously in a perturbed system downstream of a site where the perturbation is introduced.

Although one embodiment of the invention uses saline as a diluent and measures the dilution of an existing endogenous material such as blood, the method in accordance with the present invention generally contemplates measuring a parameter transcutaneously in a perturbed system downstream of a site where the perturbation is introduced. The parameter can, for example, comprise a marker and the method comprises measuring the marker downstream using a sensor. Possible markers are proteins or red cells tagged with a radio nucleotide, which can be measured using a Geiger counter. Other parameters that can be measured in accordance with the present invention, and the devices for measuring them are: ultrasound, measured by an ultrasound detector; temperature, measured by a thermistor; impedance, measured by a bio-impedance measuring device; and albumen, glucose, and other blood constituents, measured using the optical sensor disclosed herein, but in which the LEDs emit different wavelengths suited to the specific constituent.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIGS. 5–12 are graphical representations of a full test matrix performed using the model of FIG. 3 and the $TQ_a$ method of the invention.

DETAILED DESCRIPTION OF THE PREFERRED EMBODIMENTS

Figure 1:
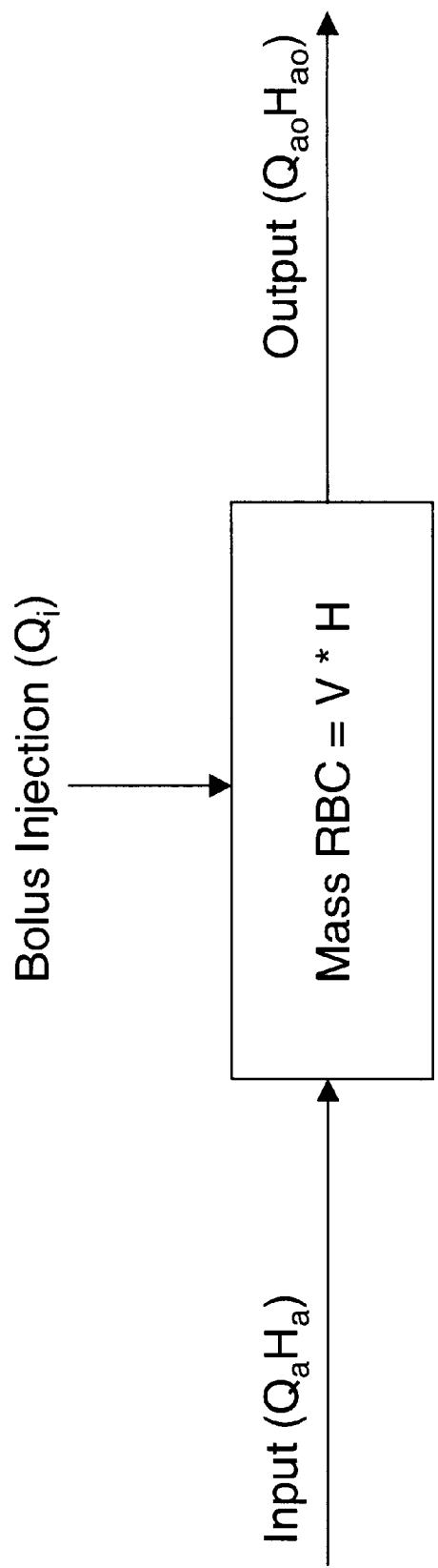
FIG. 1 is a diagrammatic view of a basic red blood cell mass balance model of an access site for a typical hemodialysis patient.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The following abbreviations and variables are used throughout the present disclosure in connection with the present invention:

AV = arteriovenous
α = access region optical attenuation coefficient
$\alpha_o$ = non-access bearing region optical attenuation coefficient
$B_o$ = composite of all the non-access region S, K coefficients
C = proportionality scalar
d = distance between the emitter and the detector
H = hematocrit, generally
$H_a$ = access site hematocrit
$H_{ao}$ = hematocrit beneath the sensor (outside the dialyzer)
$H_i$ = hematocrit of normal saline
ΔH = change in hematocrit ($H_a - H_{ao}$)
i = intensity of light, generally
$I_{baseline}$ = baseline measured intensity (taken in the absence of a bolus)
$I_{measured}$ = light back-scattered from a turbid tissue sample
$I_o$ = emitted radiation intensity
K = bulk absorption coefficient
$K_b$ = access blood absorption coefficient
Q = blood flow
$Q_a$ = access blood flow
$Q_{ao}$ = output blood flow of the access site between the venous portion of the access site and into the vascular system
$Q_b$ = dialyzer pump flow rate
$Q_i$ = average flow rate at which diluent bolus is injected into the access site
$Q_h$ = flow rate of the heart (cardiac output)
$RBC_{in}$ = red blood cell mass flowing into the access site
$RBC_{out}$ = red blood cell mass flowing out from the access site
S = bulk scattering coefficient
SNR = signal-to-noise ratio
$V_a$ = net volume of blood in the access site during the time interval, t
$V_{ao}$ = volume of access blood plus indicator volume
$V_i$ = specific volume of an indicator diluent infused into the access site
$X_b$ = percentage of the access volume to the total volume illuminated (access blood proration value)

I. Introduction

The novel transcutaneous ABF ($TQ_a$) measurement technique that is the subject of the present invention provides a straightforward method of determining ABF without the limitations of previous methods. Much like other transcutaneous measurements, such as oxygen saturation, hematocrit, and glucose, it is based upon optical techniques. The $TQ_a$ approach continuously measures the percentage change in hematocrit or another blood parameter (either macroscopic or microscopic) resulting from a bolus of saline (or other diluent) injected into the patient's access site, which typically is in the form of an arteriovenous graft or fistula. In turn, using the Ficke dilution principle, and more specifically, the Henriques, Hamilton, Bergner principle, an access blood flow rate value is determined.

II. Model and Theory

FIG. 1 illustrates a basic red blood cell mass balance model of a typical hemodialysis patient access site. Blood flows into the access site from an arterial source at a flow rate $Q_a$ and constant hematocrit value $H_a$. The magnitude of this inflow is primarily determined by the hemodynamics of the patient and the status of the access site itself. The hematocrit of the blood flowing into the shunt portion of the access site is typical of the bulk blood flow of the cardiovascular circuit, and for short time durations (less than 1 minute) this hematocrit may be considered as a constant. The red blood cell (RBC) mass flowing into the access site is, $$RBC_{in} = Q_a H_a = \frac{\partial V_a}{\partial t} H_a \quad (1)$$

A bolus injection port is used to infuse a specific volume ($V_i$) of an indicator diluent into the access site. Normal saline whose red cell content or hematocrit is zero ($H_i = 0$) is typically used. However, the indicator diluent does not have to be saline, but can also, for example, be a dye or another liquid having a hematocrit of zero.

The diluent bolus is injected into the access site at an average flow rate of $Q_i$, $$Q_i = \frac{\partial V_i}{\partial t} \quad \text{(bolus injection flow rate)} \quad (2)$$

The output blood flow from the shunt portion of the access site into the venous portion of the access site and into the vascular system, $Q_{ao}$, is the nodal sum of the two inflow rates, $Q_a$ and $Q_i$, where $$Q_{ao} = \frac{\partial V_{ao}}{\partial t} = \frac{\partial V_a}{\partial t} + \frac{\partial V_i}{\partial t} \quad \text{(flow balance equation)} \quad (3)$$

and the outgoing red blood cell mass flow from the access site is $$RBC_{out} = Q_{ao} H_{ao} = \frac{\partial V_{ao}}{\partial t} H_{ao} \quad (4)$$

Since the hematocrit of the indicator solution is zero, the RBC mass does not change and therefore the RBC mass balance becomes:

$$RBC_{in} - RBC_{out} = \frac{\partial (VH)}{\partial t} = 0 \quad (5)$$

or, $$\frac{\partial V_a}{\partial t} H_a = \frac{\partial V_{ao}}{\partial t} H_{ao} \quad \text{(mass balance equation)} \quad (6)$$

Equations (3) and (6) may be combined to yield $$\frac{\partial V_a}{\partial t} H_a = \left(\frac{\partial V_a}{\partial t} + \frac{\partial V_i}{\partial t}\right) H_{ao} \quad (7)$$

or, $$\frac{\partial V_a}{\partial t}(H_a - H_{ao}) = \frac{\partial V_i}{\partial t} H_{ao}$$

and finally, $$\frac{\partial V_a}{\partial t}\left(\frac{\Delta H}{H}\right) = \frac{\partial V_i}{\partial t} \quad (TQ_a \text{ differential equation of state}) \quad (8)$$

The $TQ_a$ differential equation of state may be re-written in a transient (that is, a time dependent) formulation or a steady flow formulation.

The transient formulation is derived by substituting $$Q_a = \frac{\partial V_a}{\partial t}$$

into equation (8) and integrating, which yields:

$$Q_a = \frac{V_i}{\int F\left(\frac{\Delta H}{H}\right) dt}, \quad \text{where} \quad \frac{\Delta H}{H} = \text{a function of time} \quad (9)$$

The steady flow form of the $TQ_a$ differential equation is obtained by assuming uniform and steady flow rates over the analysis time period. In this case, the net access blood flow rate $Q_a$ is assumed to be $$\frac{\partial V_a}{\partial t}$$

and the injection inflow rate $$\frac{\partial V_i}{\partial t} = Q_i$$

is assumed to be uniform and steady. Therefore, $$Q_a = \frac{Q_i}{\frac{\Delta H}{H}} \quad \text{(the steady flow formulation)} \tag{10}$$

In both cases, the quantity $$\frac{\Delta H}{H} \text{(the percentage change in the access hematocrit)}$$

is measured as the indicator bolus is injected into the system. If the injection rate $Q_i$ is uniform and constant, then the access flow $Q_a$ may be determined from the steady flow formulation (10). Conversely, if the system remains dynamic and the bolus injection rate is uncertain or uncontrollable, then the transient solution (9) must be used to determine $Q_a$. In a practical sense, it may be easier to control the bolus volume as opposed to the rate of injection. In vitro tests have been conducted that show the two methods to be equivalent, as discussed below.

Determination of $$F\left(\frac{\Delta H}{H}\right)$$

The percentage change in blood parameters (both macroscopic and microscopic) passing through the access site can be measured in a variety of ways. Macroscopic parameters such as bulk density or flow energy can be measured by ultrasonic, temperature, or conductivity means. Microscopic parameters (sometimes called "physiologic or intrinsic" parameters) such as hematocrit or red cell oxygen content are measured by optical means. Each technique has its respective advantages and disadvantages, both rely on the quantity $$F\frac{\Delta H}{H}.$$

Figure 2:
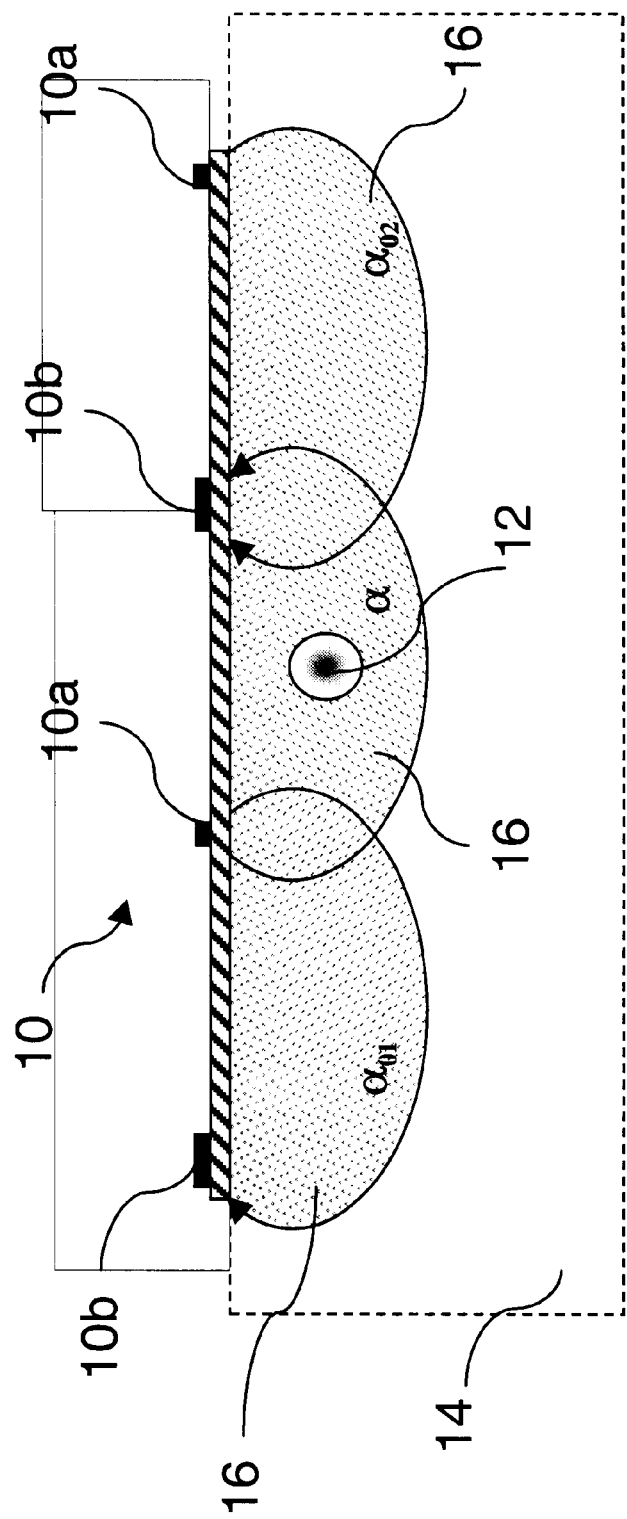
FIG. 2 is a diagrammatic view illustrating the illuminated volumes or "glowballs" produced by the emitters and seen by the detectors of a sensor used to measure $TQ_a$ with the method of the invention.

Inherent in all of these is the need to differentiate the access site, and parameter changes therein, from the surrounding tissue structure. Because of the complicating factors associated with the tissue structure of the access site, most previous methods (with exception of color Doppler) have generally been limited to extracorporeal evaluation within the dialysis delivery circuit which is attached to the access site during hemodialysis. The method in accordance with the present invention is not limited to the extracorporeal circuit but rather utilizes a transdermal optical sensor 10 positioned directly over the access site 12 itself and is based upon optical back-scattering of monochromatic light ($\lambda$=805 nm–880 nm) from the blood flow in the access site 12 and the surrounding tissues 14. As shown in FIG. 2, the sensor 10 incorporates complementary photoemitters (such as LEDs) 10a and photodetectors 10b, and may be of the type described in co-pending application Ser. No. 09/750,076, entitled "Sensor For Transcutaneous Measurement of Access Blood Flow," filed on even date herewith (Dec. 29, 2000), which is incorporated herein in its entirety.

Preferably, the optical sensor 10 comprises an LED of specific wavelength and a complementary photodetector. A wavelength of 805 nm–880 nm is used because it is near the known isobestic wavelength for hemoglobin, is commercially available, and has been shown to be effective in the optical determination of whole blood parameters such as hematocrit and oxygen saturation.

When the sensor is placed on the surface of the skin, the LED illuminates a volume of tissue, and a small fraction of the light absorbed and back-scattered by the media is detected by the photodetector. As shown in FIG. 2, while light travels in a straight line, the illuminated volume as seen by the photodetector can be visualized as an isointensity ellipsoid, as individual photons of light are continuously scattered and absorbed by the media. Because a wavelength of 805 nm–880 nm is used, hemoglobin of the blood within the tissue volume is the principal absorbing substance. The scattering and absorbing characteristics are mathematically expressed in terms of a bulk attenuation coefficient ($\alpha$) that is specific to the illuminated media. The amount of light detected by the photodetector is proportional via a modified Beer's law formula to the instantaneous net $\alpha$ value of the media.

When the volume of tissue illuminated includes all or even part of the access, the resultant $\alpha$ value includes information about both the surrounding tissue and the access itself. In order to resolve the signal due to blood flowing within the access from that due to the surrounding tissues, the sensor system illuminates adjacent tissue regions on either side of the access. Values of $\alpha_o$ for tissue regions not containing the access are then used to normalize the signal, thus providing a baseline from which relative changes can be assessed in access hematocrit in the access blood flowing directly under the skin.

The present technique is related to that used in transcutaneous oxygen saturation and hematocrit measurements and requires the use of optical physics and laws associated with optical determination of physiologic elements including hematocrit.

Modified Beer's Law

Numerous studies have shown that light back-scattered from a turbid tissue sample follows a modified form of Beer's Law, $$I_{measured} = I_o A e^{-\alpha d},$$

where $A \approx \alpha$
where $I_o$ is the radiation intensity emitted from the LED, A is a complex function of d and $\alpha$, d is the distance between the LED and detector, and $\alpha$ is the bulk optical attenuation coefficient. The $\alpha$ term is a function of the absorption and scattering nature of the tissue and has a strong dependence on hematocrit, and can be computed as:

$$\alpha \approx \frac{-\text{Ln}\left(\frac{I_{measured}}{I_o}\right)}{d} \tag{12}$$

or from equation (11), $\alpha$ in a polynomial form.

Compartmentalization of $\alpha$

A transcutaneously measured a value is actually a prorated composite measure of all the absorption and scattering elements contained within the illuminated volume or "glowball" 16 of the emitter source 10a (see FIG. 2), and typically includes the effects of tissue, water, bone, blood, and in the case of hemodialysis patients, the access site 12. In the determination of α, clearly only the blood flowing through the access site 12 is of interest. The task therefore becomes one of separating the effects of absorption and scattering of the access site 12 from that of surrounding tissue structure 14. Starting with the well known definition, $$\alpha = \sqrt{3K(K+S)} \quad (13)$$

where K is the bulk absorption coefficient and S is the bulk scattering coefficient, and separating the access blood coefficients from non-access blood coefficients and rearranging terms, $$X_b K_b \approx \alpha^2 - B_o \quad (14)$$

where $X_b$=percentage of the access volume to the total volume illuminated
$K_b$=access blood absorption coefficient
$B_o$=composite of all the non-access region S, K coefficients Now, letting $B_o = \alpha_o^2$, we have $$X_b K_b = \alpha^2 - \alpha_o^2 \quad (15)$$

In equation (14), the access blood coefficient, $K_b$, is directly proportional to hematocrit (H), $K_b = H \cdot C$. Therefore, $$X_b \cdot H \cdot C = X_b K_b = \alpha^2 - \alpha_o^2 \quad (16)$$

To determine $\alpha_o$, measurements are made in areas near but not including the access site 12, as depicted in FIG. 2. If the tissue 14 is more or less homogenous, it is only necessary to make a single reference $\alpha_o$ measurement. On the other hand, if a gradient in $\alpha_o$ exists in the area of interest (and this is typically the case in vivo) multiple measurements are made to establish the nature of the gradient and provide an averaged estimate of $\alpha_o$.

Determination of $$\frac{di}{i}$$

The value of $$\frac{di}{i}$$

is defined as the time derivative of intensity I, normalized by I. This is expressed from equation (11) as:

$$\frac{di}{i} = X_b \cdot \Delta K_b \left(d - \frac{1}{\alpha}\right), \text{ where } A \approx \alpha$$

or, $$X_b \cdot \Delta K_b = \frac{\frac{di}{i}\alpha}{\left(d - \frac{1}{\alpha}\right)}$$

which is proportional to ΔH. Hence, $$X_b \cdot \Delta H \cdot C = X_b \cdot \Delta K_b = \frac{\frac{di}{i}\alpha}{\left(d - \frac{1}{\alpha}\right)} \quad (17)$$

To determine $$\frac{di}{i},$$

a baseline intensity (taken in the absence of a bolus) is first measured to establish a reference. The intensity is then measured as a time varying signal, I(t). The quantity $$\frac{di}{i}$$

is then calculated as $$\frac{di}{i} = \frac{I_{baseline} - I(t)}{I_{baseline}} \quad (18)$$

Final Determination of $$F\left(\frac{\Delta H}{H}\right)$$

The value $$F\left(\frac{\Delta H}{H}\right)$$

is the ratio of equations (17) and (16), $$F\left(\frac{\Delta H}{H}\right) = \frac{\frac{di}{i}}{\left(d - \frac{1}{\alpha}\right)(\alpha^2 - \alpha_o^2)} \quad (19)$$

Since d is fixed and known, $$\frac{di}{i},$$

α, and $\alpha_o$ are computed by equations (17) and (12). It is important to note that in the final ratio of $$F\left(\frac{\Delta H}{H}\right),$$

the access blood proration value, $X_b$, cancels out. This removes access size and/or volume and depth dependence from the final result. Likewise, the $$\frac{di}{i} \text{ and } \frac{\alpha}{\alpha^2 - \alpha_o^2}$$

common mode ratios eliminate skin color variations, as known in pulse oximetry.

Description of the Method

In order to use indicator dilution techniques to measure vascular access flow rates during routine hemodialysis, the indicator must be injected upstream and its concentration detected downstream in the blood flowing through the vascular access site. Reversing the dialysis blood lines during the hemodialysis treatment permits application of indicator dilution by direct injection of the indicator into the venous dialysis tubing. The $TQ_a$ method that is the subject of the present invention permits a unique application of indicator dilution principles since the sensor 10 can detect a dilution signal downstream of the venous needle through the skin. This geometry permits determination of the vascular access flow rate without reversal of the dialysis blood lines.

Figure 3:
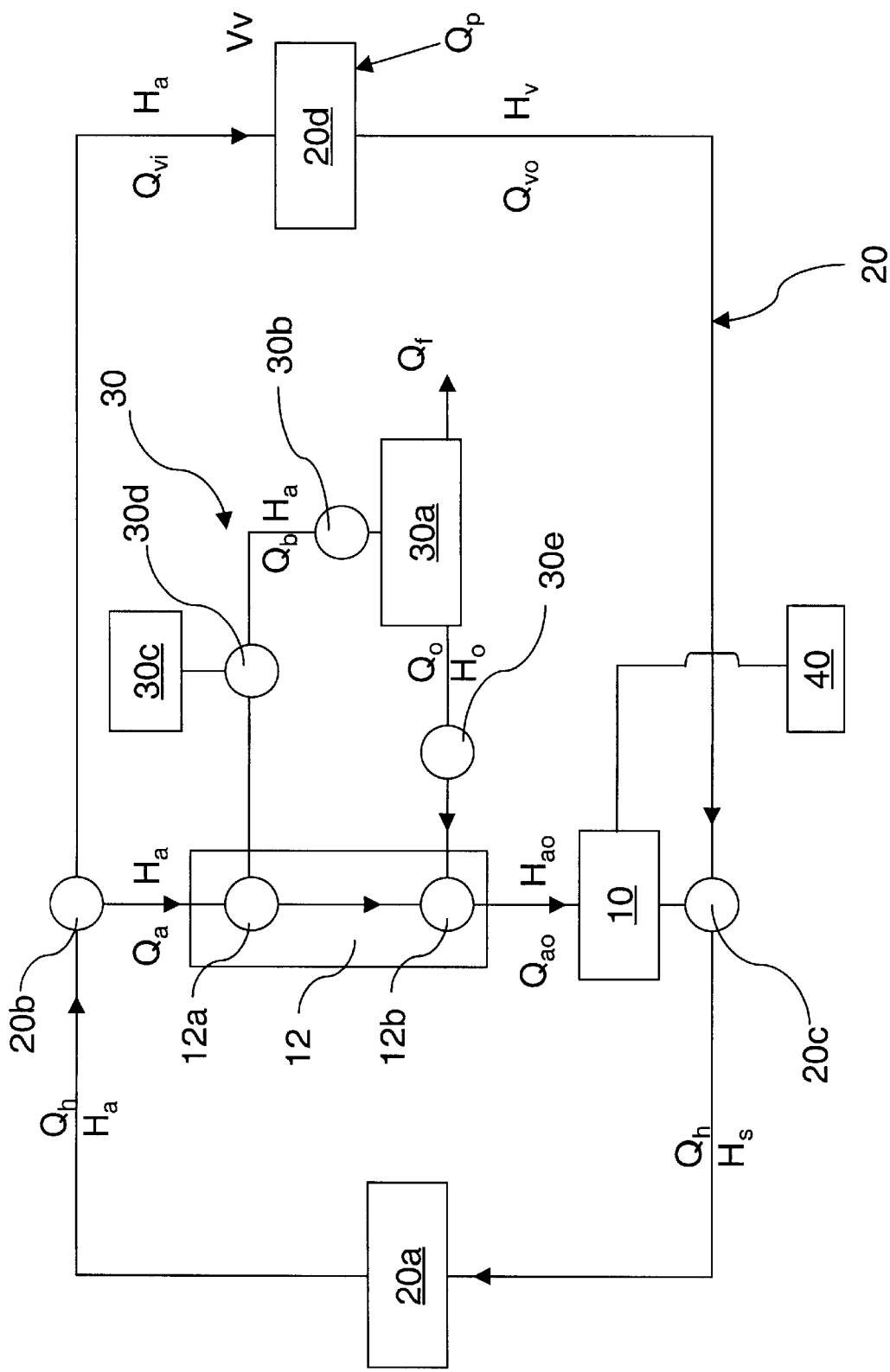
FIG. 3 is a diagrammatic view of a patient circulatory system and associated in vivo dialysis circuit in which a $TQ_a$ sensor is placed to carry out the $TQ_a$ method of the invention.

The method in accordance with the present invention will now be described in connection with the measurement of hematocrit using a transcutaneous optical sensor 10. The general environment of hemodialysis and typical components are described in detail in U.S. Pat. No. 5,351,686, which is incorporated herein by reference in its entirety. Referring to FIG. 3, there is shown a diagrammatic view of a patient cardiovascular circuit 20 and associated in vivo dialysis circuit 30 in which a $TQ_a$ sensor 10 is placed to carry out the $TQ_a$ method of the invention.

The heart volume is denoted as 20a, the access/artery connection is denoted as 20b, the access/vein connection is denoted as 20c, and the capillary bed venous pool is denoted as 20d. As is conventional, the dialysis circuit 30 incorporates a dialyzer 30a and a dialyzer ($Q_b$) pump 30b upstream of the dialyzer 30a; a saline drip bag 30c is connected to the dialysis tubing circuit 30 through a first or arterial needle port 30d inserted in the dialysis tubing circuit 30 on the arterial side between the arterial needle site 12a and the dialyzer pump 30b. Blood is taken out of a patient by a needle inserted into the hemodialysis access site 12 (a surgically implanted shunt or fistula) at the arterial needle site 12a on the "arterial" or upstream side of the dialyzer circuit 30. The arterial needle is connected to an intake catheter, so that unclean blood flows from an artery in the patient through the intake catheter to the dialyzer pump 30b. From the dialyzer pump 30b, the blood flows to the input port of the dialyzer 30a, where it is cleaned. The clean blood is returned to the patient by a return catheter connected to a needle inserted into the access site 12 at the venous needle site 12b on the "venous" or downstream side of the dialyzer 30a. The sensor 10 is positioned downstream of the diluent injection point and upstream of the fistula/vein connection 20c.

As shown in FIG. 2, the sensor 10 comprises a light source (photoemitter, e.g., an LED) 10a and a detector 10b and is placed directly on the skin over the vascular access site 12 downstream of the venous dialysis needle. The sensor 10 emits light at a wavelength of 805 nm–880 nm, near the isobestic wavelength for hemoglobin, and can accurately determine the relative changes in hematocrit in the access blood flowing directly under the skin. The fraction of light absorbed by the blood flowing through the vascular access site 12, which has been reflected by the blood and underlying tissue 14 and can be detected by the sensor 10, is proportional to the hematocrit in the vascular access site 12

(and more particularly, to the ratio $\frac{\Delta H}{H}$)

as discussed above.

The sensor 10 outputs a signal proportional to the hematocrit in the vascular access site 12 ($H_{ao}$), from which the relative change in hematocrit in the vascular access site 12 can accurately be determined. This signal is recorded by a monitoring system 40 associated with the sensor 10. The monitoring system 40 can be a computer including a computer processor and memory, and output means such as a video monitor and printer (not shown).

In a first embodiment of the method, a stable (baseline) value $H_a$ proportional to the hematocrit in the access is first obtained. Then, a known volume (V) of a reference diluent (for example, normal saline) is injected into the dialysis venous line upstream of the venous needle. The diluent reduces the hematocrit in the vascular access site 12 beneath the sensor 10 to a time-dependent hematocrit H(t) during the injection. Using the signals produced from the time the diluent is injected to the time the signal returns to the baseline value, $Q_a$ can be calculated by the monitoring system using either the transient formulation (equation (9)) or the steady state formulation (equation (10)).

A method in accordance with a second embodiment of the present invention is a method of measuring $TQ_a$ based on $Q_i \Delta T$ (the steady flow formulation, a transit time). The sensor may be of the type shown in FIGS. 2, 8, or 14 of the co-pending application.

The $TQ_a$ detector/emitter-set array is applied parallel to the flow and atop the access site 12 at $H_{ao}$ between the venous needle site 12b and the access/vein connection 20c. The $TQ_a$ array emitters can be spaced at 8, 16, 20, and 24 mm for averaging $Q_a$ and better SNR. Saline injection is achieved via the drip bag 30c and the dialyzer pump 30b or via a syringe inserted into the arterial needle port 12a. Before dialysis begins and while the AV circuit is primed with saline, the arterial line in the hemodialysis circuit is clamped off, the saline drip bag 30c is opened, and two priming flushes of two seconds duration each are infused into the shunt flow at differing blood pump flow rates of $Q_{i1}$ and $Q_{i2}$, such that the combined flow of diluted blood at $H_{ao}$ is:

$$Q = Q_a + Q_i \quad (20)$$

For example, $Q_{i1}$=100 ml/min and $Q_{i2}$=400 ml/min.

Alternately, two infusions of $Q_{i1}$ and $Q_{i2}$ are pushed at either the arterial needle port 12a or the venous needle port 12b.

As each bolus combines with the shunt flow and passes the $TQ_a$ sensor at $H_{ao}$, the transit time $\Delta T$ of the combined diluted flow ($Q = Q_a + Q_i$) is measured at $H_{ao}$ by the $TQ_a$ array.

For bolus 1:

$$Q_a + Q_{i1} = \frac{V}{\Delta T_1} \quad (21)$$

and for bolus 2:

$$Q_a + Q_{i2} = \frac{V}{\Delta T_2} \quad (22)$$

where V is the blood volume in the shunt between emitters spaced at $d_1$, and $d_2$.

Combining the two results, equations (21) and (22), and canceling V:

$$Q_a = \frac{(Q_{i2} \Delta T_2 - Q_{i1} \Delta T_1)}{(\Delta T_1 - \Delta T_2)} \quad (23)$$

Also, if V or the shunt size (diameter) is known (for example, if a new GORTEX shunt is used), a single $Q_i$ injection gives $Q_a$.

A method in accordance with a third embodiment of the present invention is a method of measuring $TQ_a$ in a hemodialysis circuit based on prime $TQ_a$. In this embodiment, a hemodialysis circuit, the priming saline volume is used as a single 10 second saline bolus when $Q_b$=300 ml/min. Preferably, the $TQ_a$ sensor is as shown in FIG. 20 of the co-pending application, is 24 mm square, and employs an outboard sensor array capable of making both parallel and perpendicular measurements. The $TQ_a$ sensor is applied over the $H_{ao}$ shunt area, preferably between the venous needle site 12b and the access/vein connection 20c, as shown in FIG. 3 in connection with the sensor 10.

Prior to the priming dilution, the $TQ_a$ sensor makes a perpendicular measurement of α of normal shunt flow. The (arterial) dialyzer $Q_b$ pump 30b is then run for 10 seconds to clear the saline. As the saline enters and mixes with the shunt flow, the second $TQ_a$ sensor 10 makes perpendicular measurements of the diluted shunt flow to determine $$\frac{di}{i}$$

and α terms.

Outboard detectors and emitters determine $α_o$ in the non-shunt, tissue area parallel to the shunt. Solving, $$Q_a = \frac{\alpha - \frac{di}{i}}{(\alpha - \alpha_o)\left(d - \frac{1}{\alpha}\right)} = \frac{k}{F\left(\frac{\Delta H}{H}\right)}, \text{ where}$$

k is a gain factor due to the electronics and is a linear function of $Q_b$ and d=the emitter-detector separation distance In the method in accordance with the third embodiment, the measurement of $α_o$ is straightforward, but its validity is dependent upon the degree of local tissue homogeneity. Also, the depth of the shunt generally requires at least 20 mm spacing between the emitter and the detector to enclose the shunt cross-section within the illuminated volume or "glowball" of the emitter and detector.

The method in accordance with the third embodiment can be used to corroborate the $Q_i$ method with $Q_i\Delta T$.

A method in accordance with a fourth embodiment of the present invention is a method of measuring $TQ_a$ based on any of the embodiments; wherein a bolus is introduced via a direct shunt injection upstream of the measurement site.

A method in accordance with a fifth embodiment of the present invention is a method of measuring $TQ_a$ based on $\Delta T$, transit time. In this embodiment, a 24 mm square $TQ_a$ sensor array employs both outboard and parallel arrays, as shown in FIG. 27 of the co-pending application. A bolus is introduced either via a direct shunt injection at the arterial needle site 12a or via a short arterial/venous circuit bolus from a drip bag 30c. The perpendicular arrays measure the transit time of the bolus at $H_{ao}$ perpendicular to the shunt or fistula. The outboard sensor arrays "size" the shunt or fistula diameter via a glowball interaction perpendicular to the shunt or fistula. $Q_a$ is then directly calculated as from transit time (velocity) and cross-sectional area.

Figure 4:
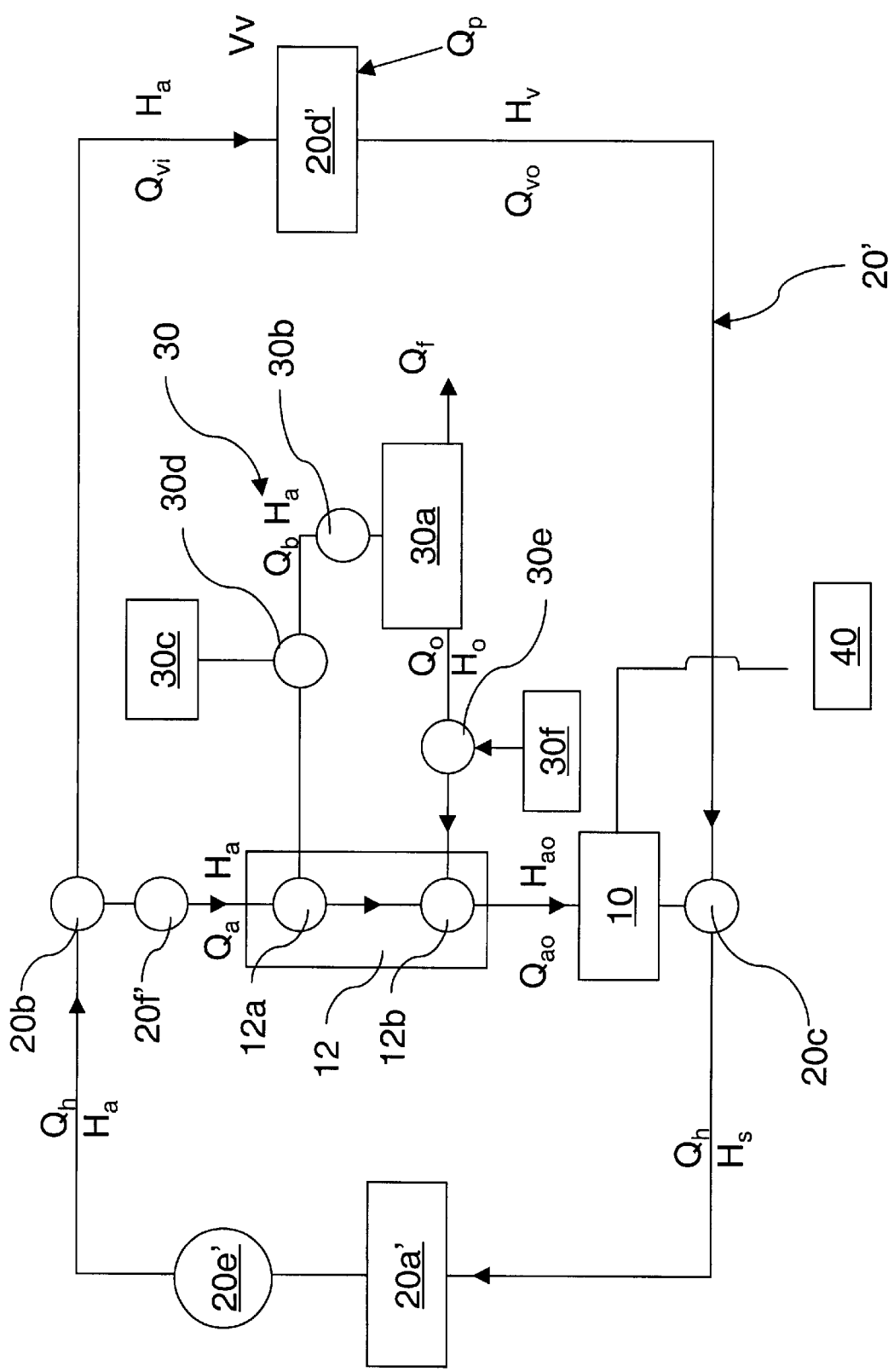
FIG. 4 is a diagrammatic view of an in vitro cardiovascular-dialysis model constructed to test the $TQ_a$ method of the invention.

Referring now to FIG. 4, there is shown an in vitro cardiovascular-dialysis model that was constructed to test the $TQ_a$ method. In the in vitro model, a patient cardiovascular circuit 20' was simulated using a 1 L central blood volume 20a', 4 L venous pool 20d', and a cardiac pump 20e' placed downstream of the central blood volume 20a'. A PT FE access site 12 was placed in a shallow tunnel cut in a piece of chicken breast muscle and covered with 15 mm of chicken skin. To complete the simulation, a $Q_a$ pump 20f' was connected to the access site 12. A typical arterial-venous dialyzer circuit 30 with a dialyzer 30a, a dialyzer ($Q_b$) pump 30b, and a drip bag 30c was connected to the access site 12 via arterial and venous needles at arterial and venous needle sites 12a and 12b, simulating hemodialysis treatment conditions. A saline injection pump 30f was also provided.

The test protocol for the in vitro model comprised the following steps:

1. Attach the sensor 10 to a reference material with known α and determine all reference I values, $i_o$.
2. Attach the sensor 10 on the chicken skin in line with the access site 12.
3. Set the cardiac pump 20e' at 3000 ml/min.
4. Stop the $Q_b$ pump 30b, clamp both ends of the dialyzer and connect the venous needle to the saline injection pump 30f. Set the saline injection pump 30f at 400 ml/min.
5. Set the $Q_a$ pump 20d' to a pre-calibrated flow rate at scale "2".
6. Start the data capturing process for 20 seconds and save the data into a file of the computer 40 associated with the sensor 10.
7. Five seconds after data capturing begins, inject saline from the saline drip bag 30c into the access site 12 for 5 seconds through the injection pump 30c.
8. Process the data with two different algorithms (the transient and the steady flow formulations) and calculate the $Q_a$.
9. Record the calculated $Q_a$ results from the computer 40.
10. Repeat step 5–9 with different pre-calibrated flow rate settings on the $Q_a$ pump 20d'.

While the cardiac output pump 20e' was running at 4–6 L/min, the $Q_a$ pump 20d' was varied from 300 to 2200 ml/min. A small 25×30 mm $TQ_a$ sensor 10 was placed on top of the chicken skin directly over the access site 12 to measure the hematocrit approximately 25 mm downstream of the venous needle and a single 5 second bolus of saline was infused at 400 ml/min ($Q_i$) directly into the access site 12.

A full test matrix was performed using the model and methodology described in the preceding paragraph. The matrix consisted of independently varying $Q_b$, $Q_a$, $Q_i$, $Q_h$, saline bolus volumes, skin and tissue thickness, access materials, access sizes and depth, skin color (melanin), and sensor geometries (distance from venous needle). A graphical representation of the stated results is shown in FIGS. 5–12, which represent a composite of 34 individual runs conducted to validate the accuracy versus a known $Q_a$ pump as reference. FIG. 5 shows the results of varying skin thickness and access depth. FIG. 6 shows the results of varying access size. FIG. 7 shows the results of varying access materials. FIG. 8 shows the results of varying the distance of the sensor from the needle. FIG. 9 shows the results of varying the blood pump rates. FIG. 10 shows the results of varying the cardiac pump rate. FIG. 11 shows the results of varying the bolus volume. FIG. 12 shows the results of varying the melanin content.

The average $TQ_a$ measurement error over the $Q_a$ range of 360 to 2200 ml/min was ±1.4%, n=34, R=0.99, p<0.001 and y=0.98+51. $TQ_a$ measurements were independent of $Q_b$, $Q_h$ access size or material, or chicken skin thickness and melanin content (which were varied during the tests).

The $TQ_a$ method in accordance with the present invention yielded very good in vitro results under a variety of conditions. The robustness of the optical approach to measure the $$F\left(\frac{\Delta H}{H}\right)$$

continuously from the saline dilution mitigated or virtually eliminated all of the traditional difficulties associated with present ABF measurements. Size and depth of the access site, placement of the dialysis needles, pump speed variations, skin color, tissue composition, and access site location and type, all had negligible or no effect on the $TQ_a$ reading, as discussed below.

A. Size and Depth of Access

Access measurements such as Doppler imaging accurately measure the velocity of the blood through the access site but are limited by volumetric uncertainties. The volume of the access site area under measure is either estimated or inferred from the image. In either case this becomes a major source of error. Additionally, geometric concerns associated with the uncertainty of the depth of the access site below the skin tend to exacerbate the volumetric estimate. However, the $TQ_a$ approach of the present invention eliminates this problem by using a percentage change of hematocrit in the access site during the dilution. As shown above in the discussion of the model and theory of the present invention, the size and depth-prorating variable, $X_b$, is ratiometrically eliminated. This cancellation makes the $TQ_a$ measurement impervious to variations in access site, size, and location. It is only necessary that a portion of the access site 12 be contained within the field of view of the optical sensor 10, as shown in FIG. 2.

B. Placement of Dialysis Needles

In reverse line ABF measurements, needle placement can become problematic. As fluid is drawn in from and returned to the access site it is susceptible to potential streaming under the laws of classical fluid dynamics, i.e. laminar flow. This streaming effect causes a certain portion of an injected bolus to pass through the system undetected and greatly bias the ABF measurement. Typically, this problem is addressed by assuring adequate needle separation and placement. The problem is in determining what is adequate and then in having sufficient latitude in needle placement under the constraints of patient physiology (that is, sufficient access length). Also needle orientation relative to the direction of blood flow can greatly affect the streaming and measurement error.

As indicated in the discussion of the model and theory of the invention, transcutaneous optical measurements indicate a net effect of all the tissue contained within the optical view. In essence, the various absorption and scattering effects of the tissue constituents are optically integrated over the entire illuminated volume, $\alpha$ or $\alpha_o$. Therefore, this optical integration eliminates the effect of streamlines and poor mixing within the shunt, since the entire region is integrated. Again it is only necessary that a portion of the access site 12 be contained within the field of view of the optical sensor 10, as shown in FIG. 2.

C. Pump Speed Variations

Measurements that rely on the interaction of the dialysis circuit with the patient's access site such as reversed line recirculation are dependent upon pump speed variations. The forward and reverse line $\Delta H$ method is dependent upon two ultrafiltration rate variations. In addition, all of these methods require that the patient be on dialysis while the ABF measurement is made.

However, because the measurement is made directly over the access site, the $TQ_a$ method does not even require the dialysis circuit. When present, the arterial or venous line may be used to provide an access port for the saline bolus injection, but a direct injection into the access site works equally well. This independence from the dialysis machine (and $Q_b$) allows greater flexibility in making ABF measurements during the interdialytic periods, in a physician's office, or in emergency situations.

D. Skin Color, Tissue Composition and Synthetic Grafts

Many studies have been conducted on the optical properties of human tissues. The result of these studies is an emerging spectral picture of how monochromatic light interacts with the various biological constituents. The key to success in making optical transcutaneous measurements is the appropriate selection of the wavelength for the desired biological constituent. For example, 660 nm and 805 nm wavelengths are desirable for pulse oximetery because of their oxygen saturation dependence and isobestic properties, respectively.

An 880 nm wavelength of light has shown a strong hematocrit dependence and it also affords good tissue penetration depth. 880 nm light is also able to penetrate hemodialysis synthetic PTFE grafts such as GORTEX. Skin color and skin blemishes, such as scars, have been shown to have little effect at 880 nm, especially when $$\frac{di}{i} \cdot \alpha$$

is the major mathematical operator, skin color is eliminated. Additionally, as explained above, alpha common mode separation, $\alpha^2 - \alpha_o^2$, eliminates any effects of skin color, tissue composition, and synthetic graft materials.

E. Access Location and Type

Generally dialysis patient access sites are grouped into two categories, native fistula and synthetic grafts. These access sites are typically located in the upper or lower arm but occasionally access sites are in legs as well. Sub-clavian catheter access sites [?] are not considered in $TQ_a$ discussions. The type and location of the access site does not effect the $TQ_a$ measurement to the extent that the access site location is discernable or palpable to the person placing the sensor 10 over the access site.

Finally, the results demonstrate that the $TQ_a$ method in accordance with the invention has potential for highly accurate and reproductive $Q_a$ measurements without line reversals. Because the saline bolus can be injected directly into the access site, it is also possible to routinely measure $Q_a$ interdialytically.

Modifications and variations of the above-described embodiments of the present invention are possible, as appreciated by those skilled in the art in light of the above teachings. For example, the method in accordance with the present invention generally contemplates measuring a parameter transcutaneously in a perturbed system downstream of a site where the perturbation is introduced. The parameter can, for example, comprise a marker and the method comprises measuring the marker downstream using a sensor. Possible markers are proteins or red cells tagged with a radio nucleotide, which can be measured using a Geiger counter. Other parameters that can be measured in accordance with the present invention, and the devices for measuring them are ultrasound, measured by an ultrasound detector; temperature, measured by a thermistor; impedance, measured by a bio-impedance measuring device; and albumen, glucose, and other blood constituents, measured using the optical sensor disclosed herein, but in which the LEDs emit different wavelengths suited to the specific constituent.

Further, the detector-emitter arrangement of the sensor 10 shown in FIG. 2 allows for precise access location, as a "flow finder," and also can be used to locate grafts and to localize veins in normal patients for more efficient canulatization. In this connection, the sensor 10 is placed directly on the skin over the approximate area of the access, graft, or vein, and values of $\alpha$, $\alpha_{o1}$, and $\alpha_{o2}$ are calculated as described above. A reference ratio, RR, is developed, where:

$$RR = \left(1 - \frac{\alpha_{o1}}{\alpha_{o2}}\right) \times 100$$

When RR<±15, then the access or graft or vein is "centered" correctly or found between the inboard LED 10*a* and the inboard detector 10*b*. Also, a signal strength (SS) indicator advises the user whether a sufficient signal is present for an accurate measurement, where $$SS = \left[\left(\alpha - \left(\frac{\alpha_{o1} + \alpha_{o2}}{2}\right)\right)\right] \times 100$$

When SS>40, then a sufficient amount of the access or graft or vein is within the illuminated volume of tissue. If RR is not <±15 (that is, if RR≧±15), or if SS is not >40 (that is, if SS is ≦40), then the sensor 10 is moved right or left (+ or −) to find the appropriate spot or location.

It is therefore to be understood that, within the scope of the appended claims and their equivalents, the invention may be practiced otherwise than as specifically described.

What is claimed is:

1. A method of transcutaneously measuring access blood flow comprising the steps of:
    infusing a specific volume ($V_i$) of an indicator diluent into a patient cardiovascular circuit at an access site in the absence of a hemodialysis circuit to effect a change in a blood parameter; and
    using a transdermal sensor to measure the percent change in the parameter.

2. The method of claim 1, wherein the blood parameter is selected from the group consisting of bulk density, flow energy, hematocrit, and red cell oxygen content.

3. The method of claim 1, wherein the transdermal sensor is placed over the access site.

4. The method of claim 1, wherein the blood parameter is macroscopic.

5. The method of claim 1, wherein the blood parameter is microscopic.

6. A method of measuring a blood parameter transcutaneously in an access site of a patient comprising the steps of:
    placing on the skin of the patient a sensor having a field of view so that at least a portion of the access site is within the field of view of the sensor and the tissue surrounding the access site occupies the remainder of the field of view;
    injecting a diluent into the access site upstream of the sensor at an average flow rate, the diluent chosen to alter the blood parameter to be measured;
    measuring a first bulk attenuation coefficient of the field of view containing both the access site portion and the surrounding tissue;
    measuring a second bulk attenuation coefficient of only the tissue surrounding the access site; and
    calculating the blood parameter based on the measured first and second bulk attenuation coefficients.

7. The method of claim 6, wherein the blood parameter is Hermatocrit.

8. The method of claim 6, wherein the access site is a fistula.

9. The method of claim 6, wherein the access site is a shunt.

* * * * *